United States Patent [19]
Yang

[11] Patent Number: 5,000,854
[45] Date of Patent: * Mar. 19, 1991

[54] PROTAMINE-BASED FILTER DEVICE FOR REMOVAL OF HEPARIN FROM BLOOD SAMPLES

[75] Inventor: Victor C. Yang, Ann Arbor, Mich.

[73] Assignee: The University of Michigan, Ann Arbor, Mich.

[*] Notice: The portion of the term of this patent subsequent to Jan. 24, 2006 has been disclaimed.

[21] Appl. No.: 366,188

[22] Filed: Jun. 14, 1989

[51] Int. Cl.$^5$ ............................................. B01D 36/02
[52] U.S. Cl. ............................ 210/638; 210/206; 210/257.2; 210/259; 210/263; 210/295; 210/321.72; 210/502.1; 210/639; 210/690; 502/401; 502/404; 604/5; 604/406; 424/529; 436/178
[58] Field of Search ................... 210/206, 257.2, 259, 210/263, 295, 502.1, 321.72-321.81, 638, 690, 639; 422/45, 101, 102; 424/101; 436/177, 178; 604/4, 5, 406; 502/401, 402, 404

[56] References Cited

U.S. PATENT DOCUMENTS

| | | | |
|---|---|---|---|
| 3,933,652 | 1/1976 | Weichselbaum et al. | 210/451 |
| 4,048,064 | 9/1977 | Clark III | 210/638 |
| 4,175,182 | 11/1979 | Schmer | 536/21 |
| 4,199,502 | 4/1980 | Babson et al. | 424/101 |
| 4,381,004 | 4/1983 | Babb | 210/638 |
| 4,464,165 | 8/1984 | Pollard, Jr. | 604/5 |
| 4,483,825 | 11/1984 | Fatches | 436/178 |
| 4,500,309 | 2/1985 | Diederich et al. | 210/646 |
| 4,551,435 | 11/1985 | Liberti et al. | 210/660 |
| 4,800,016 | 1/1989 | Yang | 210/502.1 |
| 4,863,611 | 9/1989 | Bernstein et al. | 210/502.1 |

Primary Examiner—W. Gary Jones
Attorney, Agent, or Firm—Rohm & Monsanto

[57] ABSTRACT

An arrangement for collecting blood from a source of blood employs a filter chamber having a substantially predefined volume for accumulating the collected blood, and first and second access ports for receiving the collected blood and for venting the filter chamber, respectively. A protamine filter is arranged within the filter chamber, and preferably is formed of regenerated cellulose hollow fibers which have been activated with CNBr and have protamine immobilized thereon. The amount of protamine immobilized thereon is controlled in a variety of ways, prior to installation and sealing of the filter element within the filter chamber. In a practical embodiment, the first port of the filter chamber is coupled to a conventional cannula needle for communicating transdermally with a living being or through a membrane of a blood storage container. The second port is coupled to a conventional syringe which applies a suction for facilitating withdrawal of the blood. In other embodiments, the protamine is immobilized on a biocompatible polymer substrate by covalent bonding.

21 Claims, 1 Drawing Sheet

PROTAMINE-BASED FILTER DEVICE FOR REMOVAL OF HEPARIN FROM BLOOD SAMPLES

BACKGROUND OF THE INVENTION

This invention relates generally to a diagnostic aid for the removal of heparin from blood and/or plasma samples, and more particularly, to a protamine-based filter device for rapid and specific removal of heparin from blood and/or plasma samples.

Heparin, a highly sulfated mucopolysaccharide, is the most commonly used clinical anticoagulant. Its major clinical applications include, inter alia: treatment of thromboembolic patients; prophylactic treatment of high risk embolic patients; post-operative prevention of thromboembolism; and prevention of clotting and thrombus formation resulting from interventions in the circulatory system, such as cardio-vascular diagnostic procedures, catheterization, surgery of the heart and vessels, and many other procedures including extracorporeal blood circulation, such as hemodialysis, use of artificial organs and organ transplantation. Heparin is quite commonly used in medical treatment. In fact, annual production of heparin in the United States totals over 6 metric tons, or $10^{12}$ USP units, corresponding to approximately 50 million doses.

As a result of its potent anticoagulant activity, the presence of very minute amounts of heparin interferes with the accuracy of all kinetic clotting tests. Thus, it is difficult, if not impossible, to assay coagulation factors accurately. The presence of heparin also renders routine coagulation screening tests for clotting defects impossible to conduct accurately. For acutely ill, hospitalized patients receiving heparin therapy, heparin contamination in blood samples drawn through heparinized cannulae causes delays, or errors, in diagnostic evaluation of coagulation mechanism. Moreover, in plasma samples from patients being changed from heparin to coumadin therapy, heparin contamination may lead to false results indicative of resistance to coumadin therapy. Accordingly, there is present in the art a significant need for a system for neutralizing or removing heparin from blood (or plasma) samples prior to commencement of coagulation and other tests.

Conventionally, heparin is neutralized by reaction with protamine. For example, since the exact amount of heparin present in plasma samples is not known, a tedious, time-consuming protamine titration procedure is required to ensure adequate neutralization. Moreover, excess protamine or protamine-heparin complex interferes with coagulation testing and results in unpredictable testing errors. Thus, in addition to the inconvenience of this procedure, the test results are of questionable accuracy.

Another conventional approach to heparin neutralization involves the use of a microbial enzyme, heparinase, to degrade heparin. Although heparinase is currently available from Miles Scientific (Naperville, Ill.), it is extremely expensive. Additionally, heparinase is produced commercially only in small quantities for specific laboratory use and is in a relatively impure form. Thus, the use of heparinase is impractical at this point in time because large quantities of highly purified heparinase would be required for any widespread clinical use thereof.

Certain methods and procedures have been developed in an effort to remove heparin from plasma samples or to neutralize same. One known system for achieving removal employs a chromatographic technique using an ECTEOLA-cellulose (anion-exchange resin) column to remove heparin from plasma samples. However, the preparation and use of such an ion-exchange column prior to testing a plasma sample for clotting time is cumbersome, time-consuming, and inconvenient.

The known method suffers from several other serious disadvantages. In most clinical situations, only a small volume of blood is drawn from the patient for testing. However, in the known chromatographic method, a certain volume of the plasma sample is trapped in the gel matrix of the column and is not available for further use. Additionally, ECTEOLA resins lack specificity to heparin, and will disadvantageously remove other clotting factors, such as factors VIII and IX, from the plasma sample. Moreover, the method is not suitable for removing heparin from whole blood.

Other approaches to the problem of heparin removal are known in the art. One such approach employs the use of a tableted form of fibrous triethylaminoethyl cellulose (an anion-exchange resin) which is commercially available from the Organon Teknika Corporation (Durham, N.C.) under the trademark "Heparsorb." Another approach involves the formation of an insoluble protamine reaction product comprising protamine sulfate or protamine sulfate and serum albumin crosslinked with glutaraldehyde which adsorbs heparin. Although these two further approaches are more convenient than the chromatographic techniques discussed hereinabove, substantial time periods (30–50 minutes) are still required to perform the entire procedure, the steps of which include, inter alia, incubation and/or agitation of the plasma sample and heparin removal agent, and centrifugation to separate the solid reaction product with the adsorbed heparin from the plasma sample. Both of these methods require special equipment, such as a rocking aliquot mixer and a centrifuge, in order to perform the procedure properly. Moreover, triethylaminoethyl cellulose is not specific to heparin, and will thus remove other clotting factors from the plasma sample. Neither of these approaches are useful for removing heparin from whole blood. Thus, they are not suitable for preparing heparin-free blood samples for tests where whole blood is required, such as whole blood clotting time tests.

It is, therefore, an object of this invention to provide a simple, rapid and specific system for removing heparin from plasma and whole blood samples.

It is another object of this invention to provide an arrangement for removing heparin from blood products, without removing other clotting factors.

It is also an object of this invention to provide an arrangement for removing heparin from blood without impairing the ability of the blood to be tested as whole blood.

It is a further object of this invention to provide an arrangement for removing heparin from blood without requiring a large sample.

It is additionally an object of this invention to provide an arrangement for removing heparin from blood without wasting a portion of the sample.

It is yet a further object of this invention to provide an arrangement for removing heparin from blood without introducing protamine or protamine-heparin complexes into the sample.

It is also another object of this invention to provide an arrangement for removing heparin from blood without requiring the use of expensive or complex equipment.

SUMMARY OF THE INVENTION

The foregoing and other objects are achieved by this invention which provides an arrangement for collecting blood from a source of blood and removing heparin therefrom. In accordance with the invention, a filter chamber having a substantially predefined volume for accumulating the collected blood is provided with a first port for coupling to the source of blood and receiving the collected blood, and a second port for venting said filter chamber. Thus, as the blood enters the filter chamber through the first port, the content of the filter chamber, which typically may be air, is released through the second port. The filter chamber contains therewithin a filter formed of a support member which supports immobilized protamine. Preferably, the filter is arranged so as to insure communication with the accumulated blood. In this manner, the heparin contained within the blood is removed by operation of the protamine.

In one highly advantageous embodiment of the invention, a cannula needle is coupled to the first port of the filter chamber for coupling to the source of blood. The source of blood may be the blood system of a living being, or a storage container. A suction apparatus may be coupled to the second port of the filter chamber for applying a negative pressure and thereby drawing the blood to be collected into the filter chamber. In one embodiment, such a suction apparatus may be a conventional syringe having a suction cylinder coupled at one end thereof to the second port of the filter chamber, and a plunger arranged to slide sealingly therewithin.

In a specific illustrative embodiment of the invention, the filter support is formed of cellulose hollow fibers. Such cellulose hollow fibers may be of the regenerated type which is commercially available under the trademark CUPROPHAN. This commercially available material is in widespread use in hemodialyzers, such as the Travenol ST series capillary flow dialyzer and the Cordis Dow C-DAK artificial kidney.

In a practical embodiment of the invention, the fibers are arranged in bundles having a weight of approximately 3 g after having been cut to a length of approximately 15-20 cm. Both ends of the fibers are potted with epoxy. The bundle is then washed with 200 ml of 1M sodium carbonate solution, and after being placed in a hood, 50 ml of a solution containing 5-10 g of CNBr (CNBr is first prepared in acetonitrile at a concentration of 1 g/ml acetonitrile) is passed through the bundle over a period of approximately 5-10 minutes. The degree of activation can be established in accordance with a known method.

Protamine immobilization is achieved by washing the bundle with 250 ml of distilled water, 250 ml of HCl, and 250 ml of 0.1M NaHCO$_3$ solution (pH 8.3) containing 0.5M NaCl. After the washing, 15 ml of protamine solution (10 mg/ml) are circulated through the bundle at a flow rate of 5 ml/min. over a period of some 2 hours. The extent of protamine immobilization is determined by measuring the protamine concentrations before and after the immobilization procedure. After the immobilization, albumin (5 mg/ml) is introduced to the fibers in order to block the residual active groups which are not used during the immobilization. The resulting bundle contains protamine on the order of approximately between 500-1,000 USP heparin units per gram of fibers.

The resulting fiber bundles are essentially non-resistant to blood flow. The size, length, and number of fibers in the device depends upon the amount of protamine immobilized. A bundle containing protamine equivalent to about 50 USP heparin units (typically a bundle of about 50 fibers having a length of 5-7 cm) is more than adequate in the specific embodiment described herein wherein blood is drawn into the filter chamber through a cannula needle by operation of a suction syringe. In such an embodiment, the blood is drawn from the source of blood, which may be a living being, at a rate of approximately 10 sec/cc. This rate of withdrawal of the blood corresponds to that which is typically used in hospitals to collect blood specimens. In order to ensure a complete removal of heparin from the sample, the plasma/blood sample is transferred to a specimen collecting container at a slower rate of approximately 50 sec/cc. Alternatively, this can be done by drawing and transferring the sample three times at a rate of approximately 10 cc/sec.

The above-mentioned filter possesses several significant advantages. First, it allows heparin to be removed from a test sample in less than one minute. This provides at least a thirty-fold enhancement in speed over any currently available method. Second, since protamine is approved by the Food and Drug Administration for its clinical use as a heparin antidote, and since protamine is most widely used both in vitro and in vivo for heparin neutralization, the protamine-based filter should be, from a clinical standpoint, the most specific means for removing heparin. Third, all of the sample volume drawn from the deheparinization process can be recovered. There is absolutely no waste of the volume of the test sample. Fourth, the filter permits heparin to be removed, not only from plasma, but also from whole blood. This provides the significant advantage of facilitating collection of blood specimens and removal of heparin therefrom simultaneously.

In the practice of the invention, the amount of immobilized protamine can be controlled by three independent ways. First, the amount of immobilized protamine can be varied by changing the degree of activation. This can be achieved either by changing the amount of CNBr, or by adopting other activation methods. Reference to the following texts should enable one of ordinary skill in the art to devise alternative methods: I. Chibata, *Immobilized Enzymes*, Halstead Press, N.Y. (1978) and K. Mosbach, "Immobilized Enzymes," *Methods in Enzymology*, Vol. 44 (1976). Several illustrative techniques are also set forth in U.S. Pat. No. 4,800,016 issued on Jan. 24, 1989 to the inventor hereof. Second, the amount of immobilized protamine can be controlled by changing the protamine concentration in the coupling solution. Third, the period of incubation during the coupling procedure can be altered. Of course, control over the amount of immobilized protamine can be affected by implementing a combination of these methods.

After the cellulose fibers discussed hereinabove having a length of 15-20 cm have been activated and the protamine immobilized therein, the bundles can be disassembled and the fibers cut shorter in length (5-10 cm). Small bundles containing about 50 USP heparin units of protamine are made using these short fibers. The bundles are introduced in the filter chamber, potted, closed by end caps, and sealed with epoxy. In the specific illustrative embodiment described herein, one of the end caps is molded to fit a standard syringe, while the other end cap is molded to fit a standard needle. The filter is then ready for use.

In a practical embodiment of the invention, the heparin filter is connected with a needle and a 5 ml syringe. Two ml of heparinized human plasma (2 USP units of heparin/ml of plasma) is drawn through the needle, the filter, and into the syringe. The plasma sample is then transferred from the syringe through the filter, the needle, and into a test tube. The activated partial thromboplastin time (APTT) of the sample before and after the filter treatment are measured. Passing the heparinized sample through the filter twice at the rate of 10 sec/cc drops the APTT to about 10–20% of its initial value. At a rate of 30 sec/cc, the APTT returns to that of an unheparinized sample. Preliminary testing of the heparin filter using heparinized sheep whole blood shows similar results. The system of the present invention therefore is usable in removing heparin from either plasma or whole blood.

In order to ensure the complete removal of heparin from the test sample, it is suggested that the test sample be passed through the filter at a slower rate, such as 30 sec/cc. For samples to be drawn directly from a heparinized patient, in order to be convenient and not to cause discomfort to the patient, it is suggested that the blood be drawn at the conventional rate of approximately 10 sec/cc, but transferred to a collecting vial at a slower rate, illustratively 50 sec/cc. Alternatively, the sample can be drawn and transferred several times, illustratively three times at the rate of 10 sec/cc, as described hereinabove.

In accordance with a method aspect of the invention, blood is collected from a living being employing the steps of coupling an inlet port of a filter chamber to the living being; applying a suction to a vent port of the filter chamber for drawing the blood into the filter chamber through the inlet port; and subjecting the blood to a protamine filter in the filter chamber.

In a specific embodiment of the method aspect of the invention, the coupling includes communicating transdermally with the living being. Additionally, the invention includes the further step of transferring the blood through the filter chamber to a test reservoir, such as a test tube. This, as described hereinabove, enhances heparin removal.

Prior to employing the filter chamber, the method aspect of the invention employs the steps of activating the inner walls of at least a bundle of hollow cellulose fibers with CNBr; and installing the bundles of hollow cellulose fibers into the filter chamber. Persons of skill in the art, in light of the teaching herein, can make filters of various sizes, within the scope of the invention.

In accordance with a further filter aspect of the invention, a protamine filter communicates with blood for removing heparin therefrom. The protamine filter is provided with a housing for forming a filter chamber for accommodating blood, the filter chamber having first and second ports. A protamine support is installed within the housing and is provided with protamine immobilized thereon. A sealing arrangement is provided for fixing the protamine support within the housing. In a specific embodiment of the protamine filter aspect of the invention, the protamine support is formed of a bundle of hollow cellulose fibers having an inner wall which is preactivated with CNBr. As discussed hereinabove, a cannula needle and a syringe can be coupled to the filter housing at the first and second ports, respectively, whereby the instrument can be used in accordance with the description herein.

In addition to the cellulose hollow fibers discussed hereinabove, the support may comprise other configurations (tubing, disks) and other materials. In a specific embodiment of the invention, the support is a blood-compatible polymer matrix. In such an embodiment, the polymer matrix may be a selectable one of polyacrylonitrile, polysulfone, polycarbonate, polyether, polyether carbonate, ethylene vinyl alcohol, nylon, and polyurethane. Preferably the protamine is immobilized to the blood-compatible polymer matrix by covalent bonding. Such covalent bonding is effected by providing on the surface of the polymer matrix a substantial number of reactive functional groups, such as hydroxyl, amino, or carboxyl groups, which can be activated for bonding with protamine.

In the aforementioned polymer matrix embodiment of the invention, it is greatly preferred that the support material be biocompatible and stable, so as not to be chemically or enzymatically degraded by the blood. It is also preferred that the material have good flow characteristics and sufficient mechanical strength and durability, but not to the extent required in extracorporeal circulation systems.

Although the inventive filter arrangement has been described in terms of removing heparin from a sample of blood fluid, large scale filter arrangements can be devised in light of the teachings herein. In particular, the novel filter arrangement may comprise a high flow affinity column which can be used for the industrial preparation of purified heparin. Moreover, inasmuch as protamine is known to precipitate nucleic acids, such as DNA, it is also contemplated that the protamine-based filter arrangement of the present invention can be used to purify nucleic acid from a bacterial cell homogenate.

BRIEF DESCRIPTION OF THE DRAWING

Comprehension of the invention is facilitated by reading the following detailed description, in conjunction with the annexed drawing, in which the single FIGURE is a partially schematic and plan view of a specific illustrative embodiment of the invention wherein a filter chamber having the protamine filter of the present invention installed therein is coupled at respective ports to a cannula needle and standard syringe.

DETAILED DESCRIPTION

Figure 1:
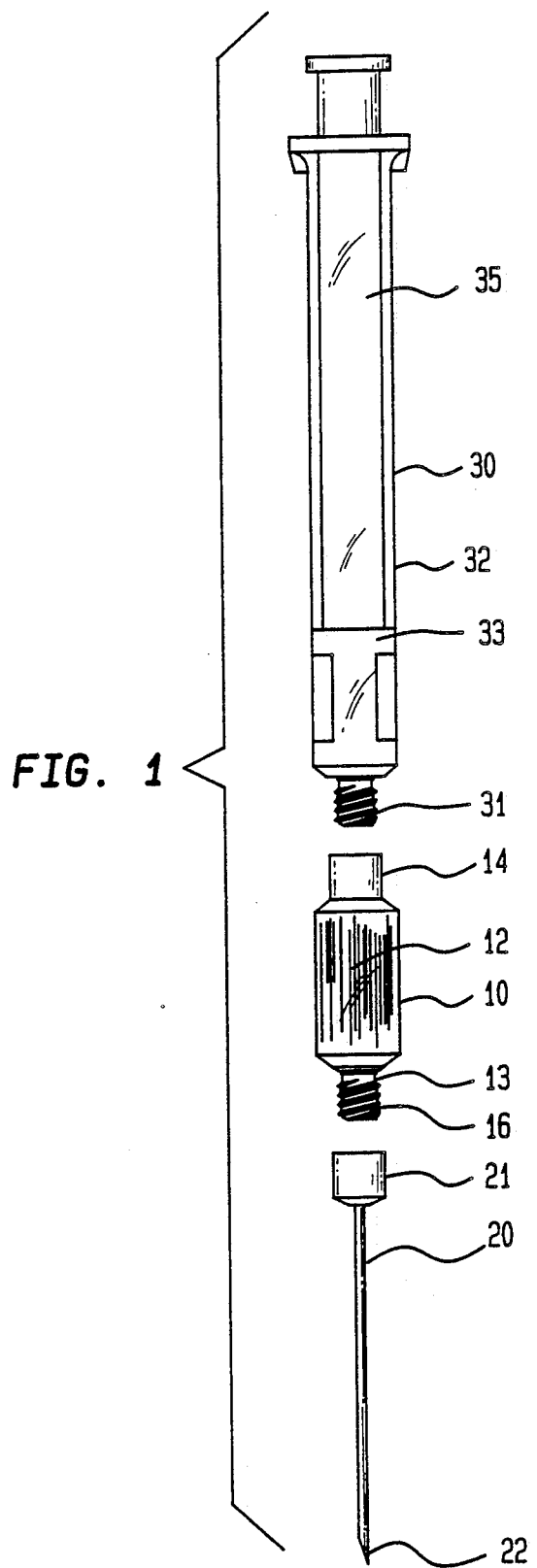

The FIGURE shows a partially schematic plan view of a specific illustrative embodiment of the invention. As shown, a filter chamber 10 having a filter element 12 therein is provided with first and second ports, 13 and 14, respectively. In this specific embodiment, filter element 12 is formed of cellulose hollow fibers which have been activated in accordance with the description hereinabove and contains immobilized protamine.

The filter chamber is coupled at its first port 13 to a needle 20 having a connector portion 21 which, in this embodiment, engages threadedly with threads 16 arranged in the vicinity of port 13. Needle 20 is provided with a sharpened portion 22 at its end distal from connector portion 21, and is provided with a conventional cannula therewithin.

Second port 14 of filter chamber 10 is arranged to couple with the syringe assembly 30. In the practice of the invention, syringe assembly 30 may be of a conventional type having a syringe coupling 31 adapted to engage with second port 14, arranged at one end of a cylinder 32. Cylinder 32 contains therewithin a plunger 33 which is arranged to slide sealingly axially along cylinder 32 in response to manipulation of a plunger rod 35. The end of cylinder 32 is distal from syringe coupling 31, and the end of plunger rod 35 distal from plunger 33 are adapted to facilitate manipulation in a conventional manner.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An arrangement for collecting a blood fluid, from a source thereof, the arrangement comprising:
   filter chamber means having a substantially predefined volume for accumulating the collected fluid, a first port for coupling to the source of fluid and receiving the collected fluid, and a second port for venting said filter chamber; and filter means formed of protamine immobilized on a support member, said filter means being disposed within said filter chamber means for communicating with said accumulated fluid.

2. The arrangement of claim 1 wherein there is further provided cannula needle means coupled to said first port of said filter chamber means, for coupling with the source of fluid.

3. The arrangement of claim 1 wherein there is further provided suction means coupled to said second port of said filter chamber means for applying a negative pressure to said filter chamber means and drawing the fluid to be collected into said filter chamber means.

4. The arrangement of claim 3 wherein said suction means comprises:
   suction cylinder means coupled at one end thereof to said second port of said filter chamber means; and
   plunger means arranged in said suction cylinder means for sliding sealingly therewithin and thereby producing said suction.

5. The arrangement of claim 1 wherein said support member of said filter means is formed of cellulose hollow fiber.

6. The arrangement of claim 1 wherein said support member of said filter means is formed of a blood-compatible polymer matrix.

7. The arrangement of claim 6 wherein said support member is formed of a selectable one of polysulfone, polycarbonate, polyether, polyether carbonate, ethylene vinyl alcohol, nylon, and polyurethane.

8. The arrangement of claim 6 wherein said protamine is bound by covalent bonding to said blood-compatible polymer matrix.

9. A method of collecting blood from a living being, the method comprising the steps of:
   coupling an inlet port of a filter chamber to the living being;
   applying a suction to a vent port of the filter chamber for drawing the blood into the filter chamber through said inlet port; and
   subjecting the blood to an immobilized protamine filter in said filter chamber.

10. The method of claim 9 wherein said step of coupling comprises the further step of communicating transdermally with the living being.

11. The method of claim 9 wherein prior to performing said step of subjecting the blood, there are provided the further steps of:
   activating inner walls of at least a bundle of hollow cellulose fibers with cyanogen bromide;
   installing said bundle of activated hollow cellulose fibers into said filter chamber; and
   subjecting said bundle to a protamine-containing solution.

12. A protamine filter for communicating with a fluid and removing therefrom a component containing a selectable one of heparin and nucleic acids, the protamine filter comprising:
   housing means for forming a filter chamber for accommodating the fluid, said filter chamber having first and second ports; and
   protamine support means having protamine immobilized thereon for removing the component, said protamine support means being disposed within said housing means.

13. The protamine filter of claim 12 wherein said protamine support means comprises a bundle of hollow cellulose fibers having an inner wall which is preactivated with cyanogen bromide.

14. The protamine filter of claim 12 wherein said fluid is blood obtained from a living being, and there are further provided:
   cannula needle means coupled to said first port of said housing means for communicating transdermally with the living being; and
   syringe means coupled to said second port of said filter housing, for drawing said blood from said living being through said cannula needle means and into said filter housing.

15. The protamine filter of claim 12 wherein said protamine support means comprises a blood-compatible polymer matrix.

16. The protamine filter of claim 15 wherein said blood-compatible polymer matrix comprises a selectable one of polyacrylonitrile, polysulfone, polycarbonate, polyether, polyether carbonate, ethylene vinyl alcohol, nylon, and polyurethane.

17. The protamine filter of claim 15 wherein said protamine is bound by covalent bonding to said blood-compatible polymer matrix.

18. The protamine filter of claim 12 further comprising seal means for fixing said protamine support means in said housing means.

19. An arrangement for collecting a blood fluid, from a source thereof, the arrangement comprising:
   filter chamber means having a substantially predefined volume for accumulating the collected fluid, a first port for coupling to the source of fluid and receiving the collected fluid, and a second port for venting said filter chamber;
   suction means coupled to said second port of said filter chamber means for applying a negative pressure to said filter chamber means and drawing the fluid to be collected into said filter chamber means, said suction means comprising suction cylinder means coupled at one end thereof to said second port of said filter chamber means and plunger means arranged in said suction cylinder means for sliding sealingly therewithin and thereby producing said suction; and filter means formed of protamine immobilized on a support member, said filter means being disposed within said filter chamber means for communicating with said accumulated fluid.

20. The arrangement of claim 19 wherein there is further provided cannula needle means coupled to said first port of said filter chamber means, for coupling with the source of fluid.

21. A protamine filter for communicating with the blood of a living being and removing therefrom a component containing a selectable one of heparin and nucleic acids, the protamine filter comprising:

housing means for forming a filter chamber for accommodating the blood fluid, said filter chamber having first and second ports;

cannula needle means coupled to said first port of said filter housing, for communicating transdermally with the living being;

syringe means coupled to said second port of said filter housing, for drawing said blood from said living being through said cannula needle means and into said housing means; and protamine support means having protamine immobilized thereon for removing the component, said protamine support means being disposed within said housing means.

* * * * *

UNITED STATES PATENT AND TRADEMARK OFFICE
CERTIFICATE OF CORRECTION

PATENT NO. : 5,000,854

DATED : March 19, 1991

INVENTOR(S) : Victor C. Yang

It is certified that error appears in the above-identified patent and that said Letters Patent is hereby corrected as shown below:

Column 1, between the title and the heading "Background of the Invention", please insert the following paragraph:

-- Government Rights

This invention was made with Government support under Grant No. 5-R29-HL38353-03 awarded by the Heart, Lung and Blood Institute of the National Institutes of Health. The Government has certain rights in the invention --.

Signed and Sealed this

Nineteenth Day of January, 1993

Attest:

DOUGLAS B. COMER

*Attesting Officer*     Acting Commissioner of Patents and Trademarks